(12) United States Patent
Birmingham

(10) Patent No.: US 11,395,742 B2
(45) Date of Patent: *Jul. 26, 2022

(54) METHOD AND DEVICE FOR JOINT REPLACEMENT

(71) Applicant: Zimmer, Inc., Warsaw, IN (US)

(72) Inventor: Patrick Birmingham, Winnetka, IL (US)

(73) Assignee: Zimmer, Inc., Warsaw, IN (US)

( * ) Notice: Subject to any disclaimer, the term of this patent is extended or adjusted under 35 U.S.C. 154(b) by 435 days.

This patent is subject to a terminal disclaimer.

(21) Appl. No.: 16/114,734

(22) Filed: Aug. 28, 2018

(65) Prior Publication Data

US 2019/0060080 A1    Feb. 28, 2019

Related U.S. Application Data

(63) Continuation of application No. 15/064,758, filed on Mar. 9, 2016, now Pat. No. 10,064,730.

(Continued)

(51) Int. Cl.
*A61F 2/34* (2006.01)
*A61F 2/36* (2006.01)
(Continued)

(52) U.S. Cl.
CPC ............. *A61F 2/3603* (2013.01); *A61F 2/32* (2013.01); *A61F 2/34* (2013.01);
(Continued)

(58) Field of Classification Search
CPC ...... A61F 2/34; A61F 2/32; A61F 2/36; A61F 2002/3408; A61F 2/3603;
(Continued)

(56) References Cited

U.S. PATENT DOCUMENTS

| 4,327,449 A | 5/1982 | Charnley |
| 4,950,299 A | 8/1990 | Noiles |

(Continued)

FOREIGN PATENT DOCUMENTS

| CA | 2960266 A1 | 9/2017 | |
| FR | 2663535 A1 * | 12/1991 | ............... A61F 2/34 |
| WO | WO-2012162571 A1 | 11/2012 | |

OTHER PUBLICATIONS

"U.S. Appl. No. 15/064,758, Examiner Interview Summary dated Jan. 12, 2018", 3 pgs.

(Continued)

*Primary Examiner* — Seema Mathew
(74) *Attorney, Agent, or Firm* — Schwegman Lundberg & Woessner, P.A.

(57) ABSTRACT

A joint replacement device is provided that includes an inner surface configured to accommodate at least one of a portion of an outer surface of a femoral head of a femur and a prosthetic secured to the femoral head, an outer surface configured to accommodate at least one of a portion of an outer surface of an acetabulum socket and a prosthetic secured to a pelvis, wherein the inner surface and outer surface each have a circular curvilinear shape and together include an inner perimeter and an outer perimeter, and wherein the inner perimeter is joined to the outer perimeter to form a posterior limb and an anterior limb, and further including, a posterior portion, an anterior portion, and a superior portion formed from the inner surface and the outer surface; wherein the superior portion further includes a posterior superior portion and an anterior superior portion.

17 Claims, 8 Drawing Sheets

Related U.S. Application Data

(60) Provisional application No. 62/133,046, filed on Mar. 13, 2015.

(51) Int. Cl.
*A61F 2/32* (2006.01)
*A61F 2/30* (2006.01)
*A61F 2/46* (2006.01)

(52) U.S. Cl.
CPC ............ *A61F 2002/30131* (2013.01); *A61F 2002/30688* (2013.01); *A61F 2002/30754* (2013.01); *A61F 2002/3208* (2013.01); *A61F 2002/3403* (2013.01); *A61F 2002/343* (2013.01); *A61F 2002/3432* (2013.01); *A61F 2002/3435* (2013.01); *A61F 2002/4635* (2013.01)

(58) Field of Classification Search
CPC ...... A61F 2002/3208; A61F 2002/3435; A61F 2002/3432; A61F 2002/344
See application file for complete search history.

(56) References Cited

U.S. PATENT DOCUMENTS

| | | | |
|---|---|---|---|
| 6,620,200 B1 * | 9/2003 | Descamps | A61F 2/34 623/22.32 |
| 8,211,184 B2 * | 7/2012 | Ries | A61F 2/34 623/22.21 |
| 8,292,954 B2 | 10/2012 | Robinson et al. | |
| 8,568,486 B2 | 10/2013 | Wentorf et al. | |
| 8,900,319 B2 | 12/2014 | Morrey et al. | |
| 8,979,935 B2 | 3/2015 | Lozier et al. | |
| 9,113,971 B2 | 8/2015 | Metzger et al. | |
| 9,278,004 B2 | 3/2016 | Shenoy et al. | |
| 9,700,420 B2 | 7/2017 | Fitz et al. | |
| 9,707,089 B2 | 7/2017 | Grey et al. | |
| 10,064,730 B2 | 9/2018 | Birmingham | |
| 10,441,684 B2 * | 10/2019 | Piecuch | A61F 2/36 |
| 10,828,169 B2 * | 11/2020 | Britton | A61F 2/4014 |
| 2001/0032021 A1 | 10/2001 | McKinnon et al. | |
| 2003/0050703 A1 | 3/2003 | Harris et al. | |
| 2003/0093152 A1 * | 5/2003 | Pedersen | A61B 17/562 623/14.12 |
| 2005/0004677 A1 | 1/2005 | Johnson | |
| 2006/0085080 A1 | 4/2006 | Bechgaard et al. | |
| 2007/0106389 A1 * | 5/2007 | Croxton | A61F 2/30942 623/22.17 |
| 2008/0208347 A1 | 8/2008 | Muratoglu et al. | |
| 2009/0005879 A1 | 1/2009 | Tuke et al. | |
| 2009/0048679 A1 | 2/2009 | Howald et al. | |
| 2009/0088865 A1 * | 4/2009 | Brehm | A61F 2/30744 606/301 |
| 2009/0226068 A1 | 9/2009 | Fitz et al. | |
| 2010/0049327 A1 * | 2/2010 | Isch | A61F 2/34 623/19.12 |
| 2011/0116533 A1 | 5/2011 | Wang | |
| 2012/0083896 A1 | 4/2012 | Kellar et al. | |
| 2012/0109328 A1 | 5/2012 | Meridew | |
| 2012/0109331 A1 | 5/2012 | Meridew et al. | |
| 2012/0319332 A1 * | 12/2012 | Mcminn | A61L 27/505 264/494 |
| 2013/0131823 A1 | 5/2013 | Morrey et al. | |
| 2014/0031948 A1 | 1/2014 | Birmingham | |
| 2015/0245913 A1 * | 9/2015 | Morrey | A61F 2/34 623/22.29 |
| 2015/0342740 A1 * | 12/2015 | Boedo | A61F 2/32 623/22.15 |
| 2016/0175099 A1 * | 6/2016 | Forsell | A61F 2/34 623/22.21 |
| 2016/0262897 A1 | 9/2016 | Birmingham | |
| 2019/0167444 A1 * | 6/2019 | Behzadi | A61F 2/34 |
| 2021/0059823 A1 * | 3/2021 | Goodman | A61F 2/4241 |

OTHER PUBLICATIONS

"U.S. Appl. No. 15/064,758, Non-Final Office Action dated Apr. 10, 2017", 15 pgs.

"U.S. Appl. No. 15/064,758, Non-Final Office Action dated Oct. 17, 2017", 15 pgs.

"U.S. Appl. No. 15/064,758, Notice of Allowance dated May 22, 2018", 9 pgs.

"U.S. Appl. No. 15/064,758, Response filed Jan. 10, 2018 to Non-Final Office Action dated Oct. 17, 2017", 14 pgs.

"U.S. Appl. No. 15/064,758, Response filed Jul. 7, 2017 to Non-Final Office Action dated Apr. 10, 2017", 6 pgs.

U.S. Appl. No. 15/064,758 U.S. Pat. No. 10,064,730, filed Mar. 9, 2016, Method and Device for Joint Replacement.

* cited by examiner

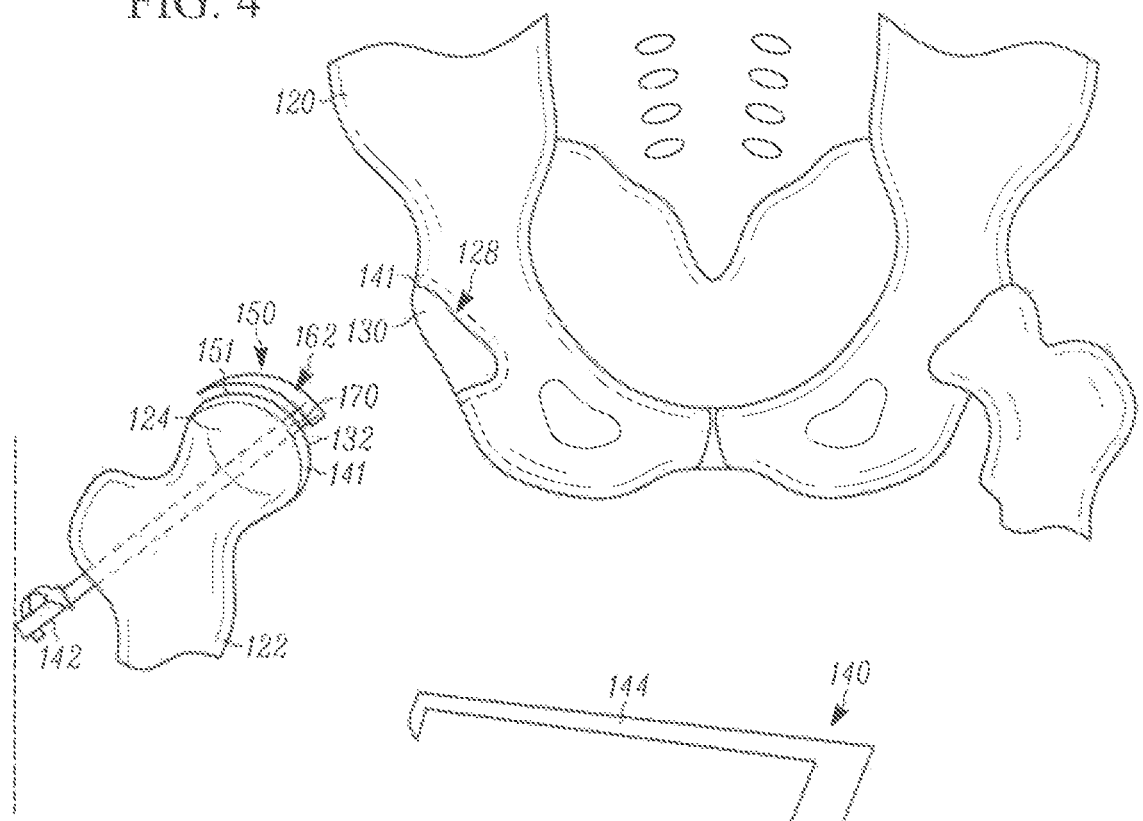
FIG. 4
FIG. 5
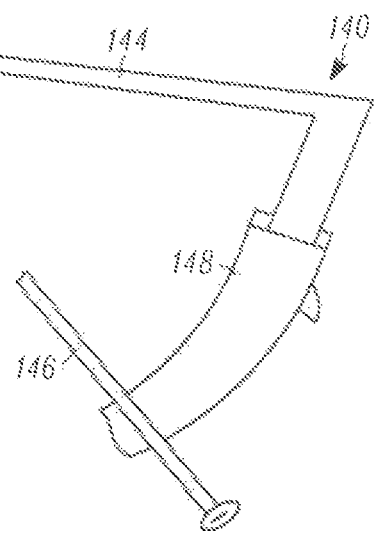
FIG. 7
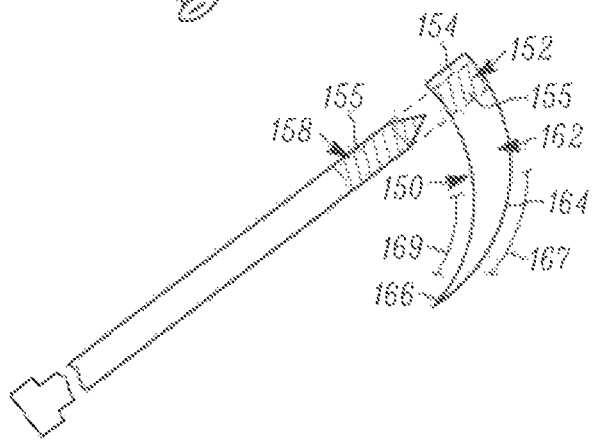
FIG. 6

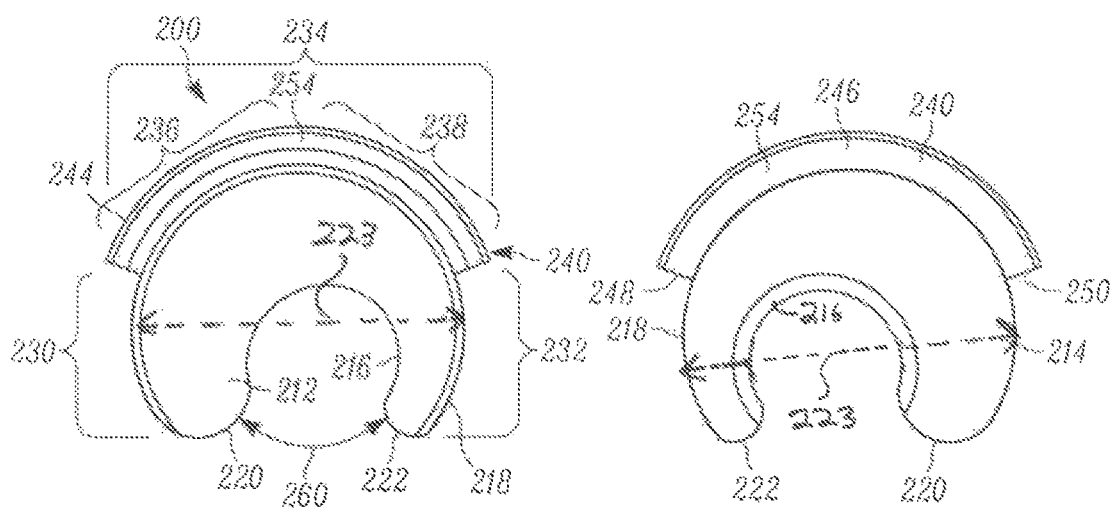
FIG. 15   FIG. 16
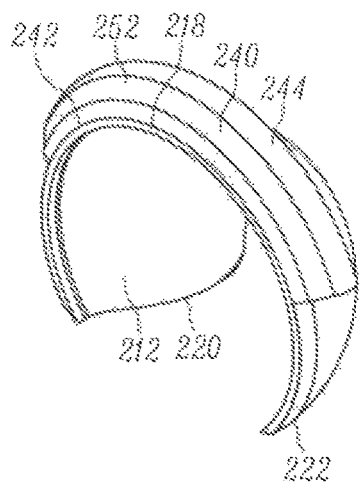 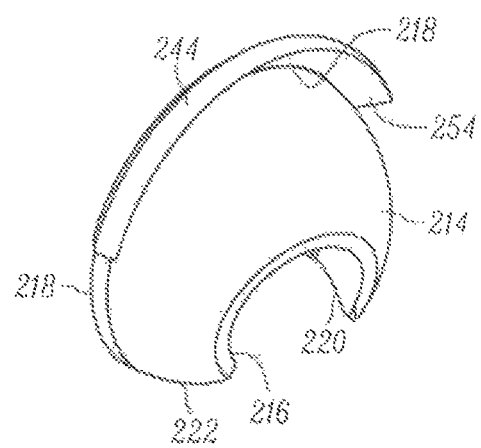
FIG. 17   FIG. 18
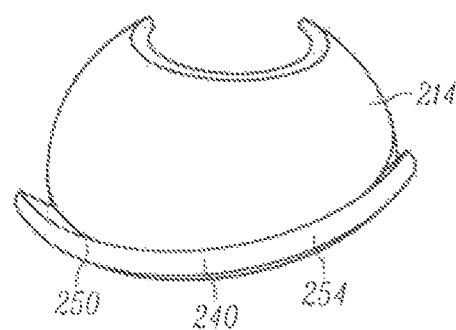
FIG. 19

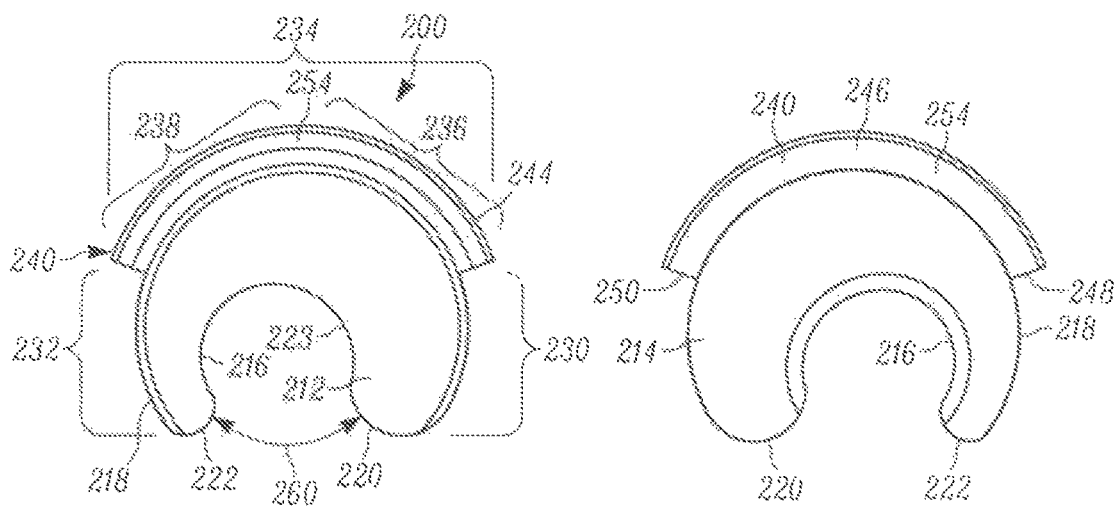
FIG. 20  FIG. 21
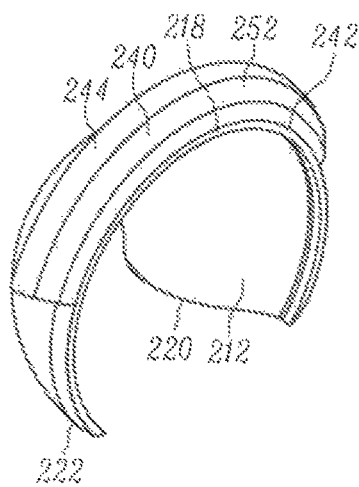 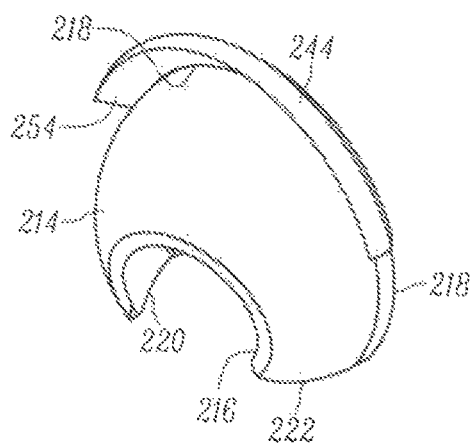
FIG. 22  FIG. 23
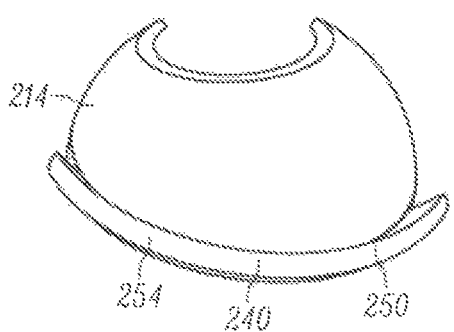
FIG. 24

METHOD AND DEVICE FOR JOINT REPLACEMENT

CROSS-REFERENCE TO RELATED APPLICATIONS

This application is a continuation of U.S. patent application Ser. No. 15/064,758, filed Mar. 9, 2016, which claims the benefit of U.S. Provisional Patent Application No. 62/133,046, filed Mar. 13, 2015, both of which are incorporated herein by reference in their entireties.

RELATED FIELD

The method and device for joint replacement relates to joint repair and replacement.

BACKGROUND

Joints provide articulation of various body parts. These joints can be damaged in numerous ways, such as exposure to trauma or degeneration due to old age or disease. Joints, such as hip joints, typically include a bone with a ball end and a bone with a socket opening. When damaged, the interaction between the ball and socket can become problematic, preventing proper articulation of a joint and/or pain in the joint. Such restriction and/or discomfort are often due to a breakdown of the surfaces of one or both of the ball and socket. In the case of a hip joint, the femur and pelvis are involved. The femur includes the femoral head with a layer of articular cartilage and the pelvic bone includes the acetabulum socket, also with a layer of articular cartilage. Once the layer of articular cartilage is worn or damaged to an advanced degree, the joint no longer functions as intended and can require surgical intervention.

Currently, to address worn or damaged hip joints, an invasive surgical procedure is performed to install a full or half prosthetic joint. The installation of the prosthetic joint involves substantial restructuring of the original joint, which requires the surgeon to inflict substantial damage to the joint area to access and install the prosthetic joint, thereby increasing the likelihood of permanent damage to surrounding nerves, ligaments, etc. In addition, this invasive procedure can result in chronic pain, poor articulation of the joint, failure of the prosthesis, etc., which can substantially decrease the likelihood of a post-operative normally functioning prosthetic joint. Often hip arthritis can cause significant discomfort, but the trauma to a patient's hip and the lingering post-operative issues can be unacceptable to a patient. In particular, if the patient is young and/or very active.

Accordingly, it would be desirable to provide a minimally invasive procedure that limits the damage to the joint area during installation and provide a more reliable prosthetic repair/replacement.

BRIEF SUMMARY

In at least some embodiments, the method of joint replacement relates to forming one or more arthroscopy portals adjacent a hip joint that includes a femur and a pelvis; inserting a guide wire through a portion of the femur to extend out of a femoral head of the femur; securing a reamer blade to the guide wire; reaming a femoral head outer surface at the end of the femoral head to at least one of access cancellous bone and remove damaged cartilage; reaming an acetabulum outer surface of the acetabulum socket of the pelvis to at least one of access cancellous bone and remove damaged cartilage; unsecuring the reamer blade from the guide wire; and inserting a hemiarthroplasty cup between the femoral head outer surface and the acetabulum outer surface.

In at least some embodiments, the method of joint replacement relates to forming one or more arthroscopy portals adjacent a hip joint that includes a femur and a pelvis; inserting a guide wire through a portion of the femur to extend out of a femoral head of the femur; securing a reamer blade to the guide wire; reaming a femoral head outer surface at the end of the femoral head to at least one of access cancellous bone and remove damaged cartilage; reaming an acetabulum outer surface of the acetabulum socket of the pelvis to at least one of access cancellous bone and remove damaged cartilage; unsecuring the reamer blade from the guide wire; rotating a cannulated drill around the guide wire and through the femur; inserting a cannulated fastener in place of the cannulated drill; inserting a cup femoral head prosthesis adjacent to the femoral head outer surface; securing the cup femoral head prosthesis to the femoral head outer surface using the cannulated fastener; and inserting a hemiarthroplasty cup between the femoral head outer surface and the acetabulum outer surface.

In at least some embodiments, the method of joint replacement relates to forming one or more arthroscopy portals adjacent a hip joint that includes a femur and a pelvis; inserting a guide wire through a portion of the femur to extend out of a femoral head of the femur; securing a reamer blade to the guide wire; reaming a femoral head outer surface at the end of the femoral head to at least one of access cancellous bone and remove damaged cartilage; reaming an acetabulum outer surface of the acetabulum socket of the pelvis to at least one of access cancellous bone and remove damaged cartilage; unsecuring the reamer blade from the guide wire; rotating a cannulated drill around the guide wire and through the femur; inserting a cannulated fastener in place of the cannulated drill; inserting a cup femoral head prosthesis adjacent to the femoral head outer surface; and securing the cup femoral head prosthesis to the femoral head outer surface using the cannulated fastener.

In at least some embodiments, a device for joint replacement relates to a prosthesis including a hemiarthroplasty cup including an inner surface and an outer surface, wherein the inner surface is shaped and sized to accommodate a reamed or unreamed femoral head outer surface, and wherein the outer surface is shaped and sized to accommodate a reamed or unreamed acetabulum outer surface of an acetabulum socket.

In at least some embodiments, a device for joint replacement relates to a prosthesis including an at least partially hemispherical-shaped cup including an inner surface and an outer surface, wherein the inner surface is shaped and sized to accommodate a reamed femoral head outer surface of a femur, and wherein the outer surface is shaped and sized to accommodate at least one of a reamed or unreamed acetabulum outer surface of an acetabulum socket and an inner surface of a hemiarthroplasty cup; a fastener securable to the femur for engagement with a portion of the hemispherical-shaped cup to provide securement of the hemispherical-shaped cup to the femoral head outer surface.

In at least some embodiments, a device for joint replacement relates to a prosthesis including a hemiarthroplasty cup including an inner surface shaped and sized to accommodate a reamed or unreamed femoral head outer surface, and an outer surface shaped and sized to accommodate a reamed or unreamed acetabulum outer surface of an acetabulum socket, wherein the hemiarthroplasty cup is configured to maintain allowance of articulation of the femoral head outer surface and the acetabulum socket relative to the hemiarthroplasty cup after implantation.

In at least some embodiments, a device for joint replacement relates to a prosthesis including an at least partially hemispherical-shaped cup including an inner surface and an outer surface, wherein the inner surface is shaped and sized to accommodate at least one of a reamed femoral head outer surface of a femur and a cup femoral head prosthesis, and wherein the outer surface is shaped and sized to accommodate a reamed acetabulum outer surface of an acetabulum socket.

In at least some embodiments, a device for joint replacement relates to a prosthesis including a cup-shaped portion including an inner surface and an outer surface, wherein the inner surface is shaped and sized to accommodate at least one of a reamed femoral head outer surface of a femur and a cup femoral head prosthesis, and wherein the outer surface is shaped and sized to accommodate a reamed or unreamed acetabulum outer surface of an acetabulum socket.

In at least some other embodiments, a joint replacement device is provided that includes an inner surface configured to accommodate at least one of a portion of an outer surface of a femoral head of a femur and a prosthetic secured to the femoral head; an outer surface configured to accommodate at least one of a portion of an outer surface of an acetabulum socket and a prosthetic secured to a pelvis, wherein the inner surface and outer surface each have a circular curvilinear shape and together include an inner perimeter and an outer perimeter, and wherein the inner perimeter is joined to the outer perimeter to form a posterior limb and an anterior limb; an interior perimeter diameter that extends between opposite sides of the inner perimeter; and a posterior portion, an anterior portion, and a superior portion formed from the inner surface and the outer surface; wherein the superior portion further includes a posterior superior portion and an anterior superior portion.

Other embodiments, aspects, features, objectives, and advantages will be understood and appreciated upon a full reading of the detailed description and the claims that follow.

BRIEF DESCRIPTION OF THE DRAWINGS

Embodiments of the method and device for joint replacement are disclosed with reference to the accompanying drawings and are for illustrative purposes only. The method and device for joint replacement is not limited in its application to the details of construction or the arrangement of the components illustrated in the drawings. The method and device for joint replacement is capable of other embodiments or of being practiced or carried out in other various ways. In the drawings:

FIG. 4 illustrates another view of the femur and pelvis of FIG. 3;

FIG. 5 illustrates an example of a drill guide;

FIG. 6 illustrates an example of a guide wire and an example of a reamer;

FIG. 7 illustrates a top view of the reamer of FIG. 6;

FIG. 15 illustrates a front view of the exemplary joint spacer;

FIG. 16 illustrates a back view of the exemplary joint spacer of FIG. 15;

FIG. 17 illustrates a front perspective view of the exemplary joint spacer of FIG. 15;

FIG. 18 illustrates a rear perspective view of the exemplary joint spacer of FIG. 15;

FIG. 19 illustrates a top view of the exemplary joint spacer of FIG. 15;

FIG. 20 illustrates a front view of the another exemplary joint spacer;

FIG. 21 illustrates a back view of the exemplary joint spacer of FIG. 20;

FIG. 22 illustrates a front perspective view of the exemplary joint spacer of FIG. 20;

FIG. 23 illustrates a rear perspective view of the exemplary joint spacer of FIG. 20; and FIG. 24 illustrates a top view of the exemplary joint spacer of FIG. 20.

DETAILED DESCRIPTION

Figure 1:
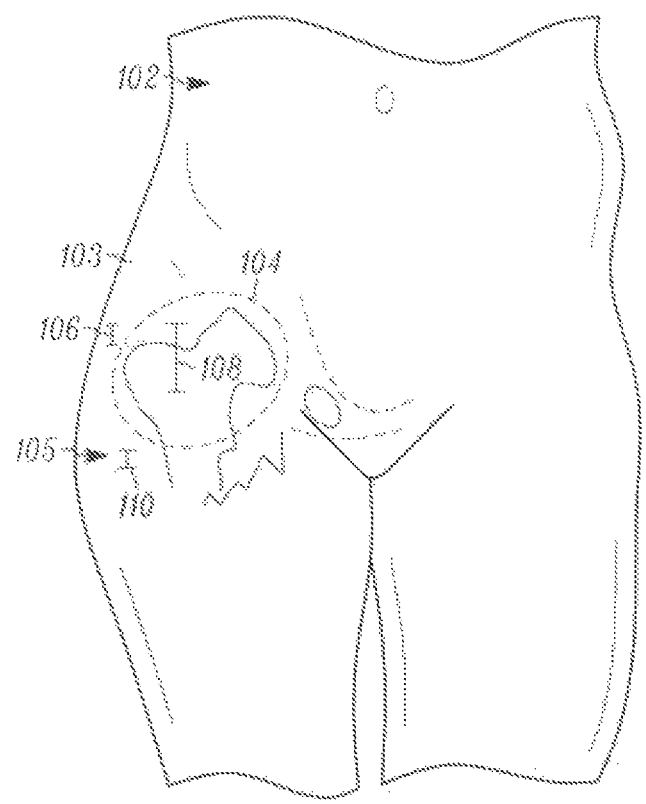
FIG. 1 illustrates a front view of a portion of an example of a human body with an example of a hip joint.

Referring to FIG. 1, a front view of a portion of an example of a human body 102 is illustrated. The body 102 is shown with a plurality of hip arthroscopy portals 105 identified. These hip arthroscopy portals 105 are provided to allow access past skin 103, muscle, ligaments, etc., to the hip joint 104 and are established as needed during a hip repair/replacement procedure. The arthroscopy portals illustrated include an anterolateral portal 106, a midanterior portal 108, and a distal anterolateral portal 110, although one or more of various other types of arthroscopy portals can be provided in place of or in addition to these portals.

Figure 2:
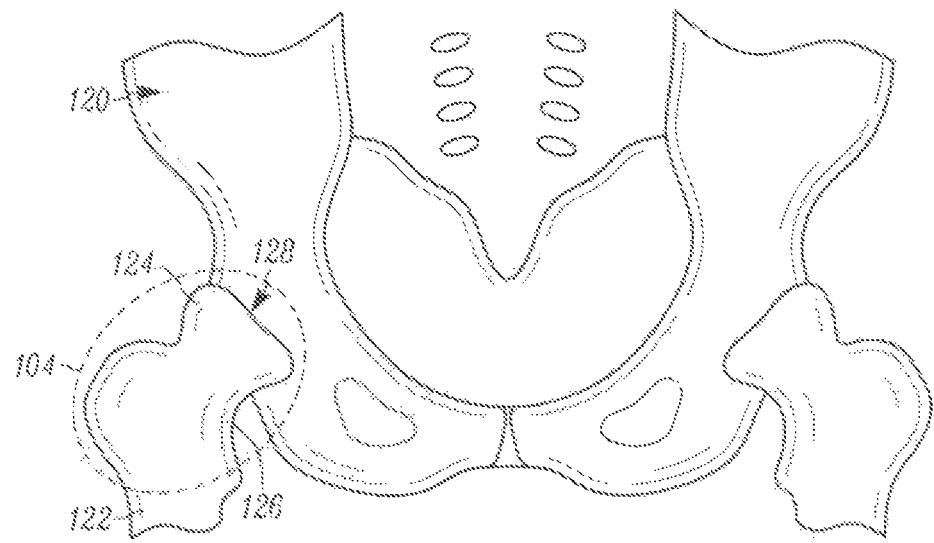
FIG. 2 illustrates an example of a front skeletal view of the hip joint of FIG. 1.
Figure 3:
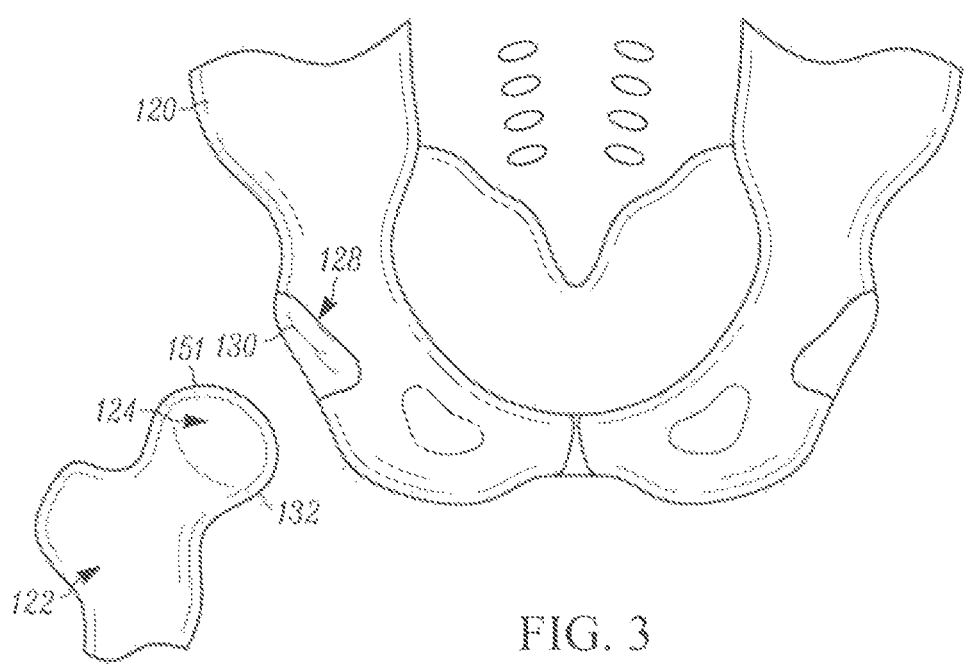
FIG. 3 illustrates a view of FIG. 2 with the femur distracted from the pelvis.

Referring to FIG. 2, a front skeletal view of the hip joint 104 is provided. The hip joint 104 includes at least portions of a pelvis 120 and a femur 122. The femur 122 includes a femoral head 124 connected to the femur 122 by a femoral neck 126. The pelvis 120 includes an acetabulum socket 128, which is a socket formed in the pelvis 120. In FIG. 2, the femoral head 124 is shown in its natural seated position in the acetabulum socket 128. FIG. 3 illustrates a view of the hip joint 104 of FIG. 2 with the femur 122 distracted from the pelvis 120. The distraction exposes an acetabulum outer surface 130 and a femoral head outer surface 132. The acetabulum outer surface 130 and femoral head outer surface 132 are at least partially comprised of a layer of articular cartilage 141 (FIG. 4).

As a result of trauma, disease, and/or degeneration, the articular cartilage 141 can become damaged resulting in a rough or irregular surface. In some cases, at least portions of the articular cartilage 141 can be substantially worn away. These conditions reduce or eliminate the normally smooth engagement of the femoral head 124 and the acetabulum socket 128. In order to provide the smooth surfaces desired for proper joint function, one or both of the acetabulum outer surface 130 and femoral head outer surface 132 are at least one of, resurfaced for engaging with a prosthesis or at least partially covered with a prosthesis. This can be achieved through at least the use of the procedures and prosthesis as described below.

Referring now to FIG. 4, another view of the hip joint 104 of FIG. 3 is illustrated. It is not evident by the illustrations, but it is to be understood that one or both of the acetabulum socket 128 and femoral head 124 can be damaged or otherwise in need of repair or replacement. The procedure described below can include the use of one or more of various tools as described below. FIG. 5 illustrates a drill guide 140 utilized for inserting a guide wire 142 (FIG. 4) into the femur 122. The drill guide 140 includes an aiming arm 144 and a drill sleeve 146, both interconnected by a handle 148. In addition, referring to FIGS. 6 and 7, a reamer 150 is provided for resurfacing an end 151 of the femoral head outer surface 132 and/or acetabulum outer surface 130. The reamer 150 is shown as sickle-shaped, although it is contemplated that the shape and size of the reamer 150 can be modified as needed to accommodate various bone and prosthesis shapes and sizes. A fastening portion, such as a locking aperture 152 can be provided at a base portion 154 of the reamer 150. The locking aperture 152 is configured to be securable to the guide wire 142. The securement can be accomplished by one or more of various methods, such as providing reverse threads 155 in the locking aperture 152 for rotational engagement with reverse threads 155 on a guide wire end portion 158. In addition, the reamer 150 includes an engagement portion 162 having a top edge 164 and bottom edge 166. The top edge 164 includes a radius of curvature 167 shaped to conform to a desired shape for the acetabulum outer surface 130. The bottom edge 166 includes a radius of curvature 167 shaped to conform to a desired shape for the end 151 of the femoral head outer surface 132. Further, the engagement portion 162 can be tapered as it extends away from the base portion 154. In at least some embodiments, the top edge 164 and bottom edge 166 each comprise a bladed edge, although other shapes and configurations can be utilized to provide the desired resurfacing effect.

In at least some embodiments, to begin a hip joint repair or replacement procedure, a patient is positioned on a hip arthroscopy traction table, in a supine, lateral, or other position as desired. The hip is distracted, as illustrated in FIG. 4, to provide the necessary access to the femur 122 and acetabulum socket 128. The hip arthroscopy portals 105 are formed as necessary, as shown in FIG. 1. Upon entry into the body 102, the hip ligamentous capsule (not shown) is cut to provide the necessary access, for example from a 10 o'clock to 2 o'clock position. The drill guide 140 is then placed through the distal anterolateral portal 110 or others as desired, and the drill sleeve 146 is pushed to the skin 103. After a small incision is made, the guide wire 142 is advanced through the femur 122 by a drill (not shown) to its aimed location (determined by the positioning of the aiming arm 144 and drill sleeve 146), which is the center 170 of the femoral head 124. After installation of the guide wire 142, the drill guide 140 is removed and the midanterior portal 108 is enlarged to provide greater access, such as to a diameter of about 4 centimeters, or other necessary size. The guide wire 142 is now positioned to receive the reamer 150. The reamer 150 is inserted through the midanterior portal 108 and positioned so the reverse threads 155 of the guide wire 142 rotationally engage the reverse threads 155 of the locking aperture 152 to allow the reamer 150 to be locked to the guide wire 142.

The drill is secured to the guide wire 142 and energized to rotate the guide wire 142. As the guide wire 142 rotates, the secured reamer 150 also rotates. Placing a pulling tension on the guide wire 142, such that the bottom edge 166 of the rotating reamer 150 engages the end 151 of the femoral head outer surface 132, serves to ream down the end 151 of the femoral head outer surface 132 at least partially to cancellous bone and/or to remove damaged cartilage, thereby partially, substantially, or completely removing the articular cartilage layer from the femoral head 124. The radius of curvature 167 along the bottom edge 166 of the engagement portion 162 can be chosen to form the end 151 of the femoral head outer surface 132 to a desired shape, such as a symmetrical hemispherical shape. Similarly, advancing (pushing tension) the guide wire 142 during rotation, such that the top edge 164 of the rotating reamer 150 engages the acetabulum outer surface 130, serves to ream down the acetabulum outer surface 130 at least partially to cancellous bone and/or to remove damaged cartilage, thereby partially, substantially, or completely removing the articular cartilage layer from the acetabulum socket 128. The radius of curvature 167 along the top edge 164 of the engagement portion 162 can be chosen to form the acetabulum outer surface 130 to a desired shape, such as a symmetrical hemispherical shape. Upon completion of the reaming process, the reamer 150 is then secured and the guide wire 142 is reversed in direction to disarticulate the guide wire 142 from the reamer 150. The reamer 150 is then removed from the body 102. Therefore, use of the reamer 150 as described, can serve to prepare the femoral head 124 and the acetabulum socket 128 for receiving or otherwise engaging each other or a prosthesis.

Figure 8:
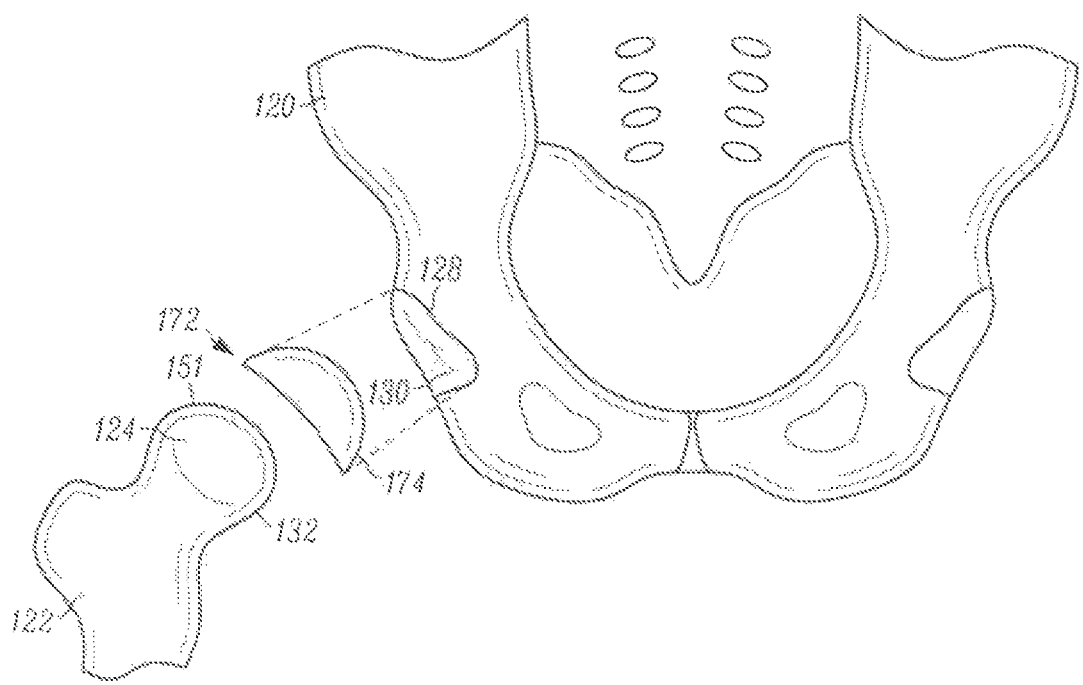
FIG. 8 illustrates the femur and pelvis of FIG. 3 and an example of a hemiarthroplasty cup prosthesis.
Figure 9:
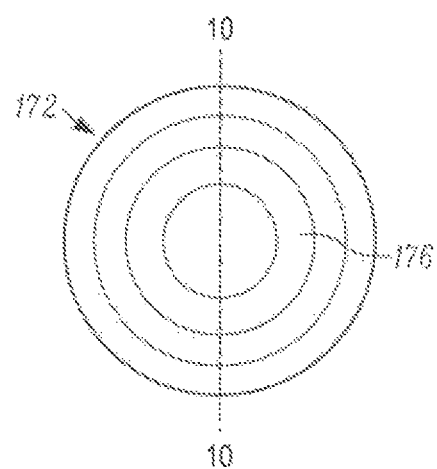
FIG. 9 illustrates a bottom view of the hemiarthroplasty cup prosthesis.
Figure 10:
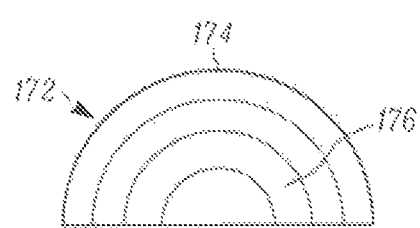
FIG. 10 illustrates a cross-sectional side view of the hemiarthroplasty cup prosthesis taken at line 10-10.

After completing the above procedure, various options exist for repairing or replacing the hip joint 104. Referring to FIG. 8, in at least one embodiment, where a hemiarthroplasty (half joint replacement) is desired, the guide wire 142 can be removed and a hemiarthroplasty cup 172 is inserted through the midanterior portal 108. The hemiarthroplasty cup 172, as seen in FIGS. 8, 9, and 10, is in at least some embodiments, a dual-sided hemispherical cup having a cup outer surface 174 and a cup inner surface 176. The hemiarthroplasty cup 172 can in at least some embodiments, be hemispherical, partially hemispherical, or substantially hemispherical, or otherwise sized to accommodate a reamed or unreamed joint bone. In addition, the hemiarthroplasty cup 172 can include alternate shapes, for example, an oblong/oval hemisphere. The cup outer surface 174 is shaped and sized to pivotably engage the acetabulum outer surface 130 and can be installed without the use of an assisting fixation method, such as cement, fasteners, bone growth agents, etc. Similarly, the cup inner surface 176 is shaped and sized to pivotably engage and articulate with the femoral head outer surface 132 (or another prosthesis installed thereon) and can be installed without the use of an assisting fixation method, such as cement, fasteners, bone growth agents, etc.

As the cup outer surface 174 can be installed without fixation, the femoral head 124 and the acetabulum socket 128 are allowed to articulate with the respective inner and outer cup surfaces 176, 174 of the hemiarthroplasty cup 172. The need for assistive fixation methods are substantially reduced or eliminated due to, at least in part due to, the minimal violation of the hip joint area during installation. For example, the above procedure does not require cutting the entire ligamentous hip capsule (not shown) or significant cutting of the musculature of the hip, in order to prepare the hip joint 104 and install the hemiarthroplasty cup 172. The limited violation can maintain sufficient structure to support and secure the hemiarthroplasty cup 172 as needed. In at least some embodiments, the hemiarthroplasty cup 172 can be secured using assistive fixation methods, such as repair or reconstruction of the ligamentous capsule, or repair or reconstruction of the acetabular labrum, or another method as desired or necessary for one or more reasons.

Figure 11C:
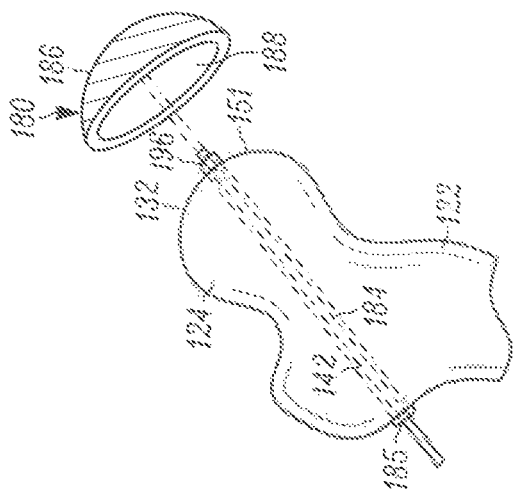
FIG. 11C illustrates the femur of FIG. 3 with an example of a cup femoral head prosthesis and an example of a cannulated fastener positioned therein.
Figure 11B:
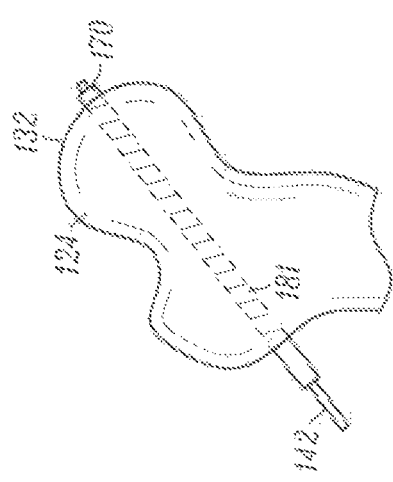
FIG. 11B illustrates the femur of FIG. 3 with an example of a cannulated drill positioned therein.
Figure 11E:
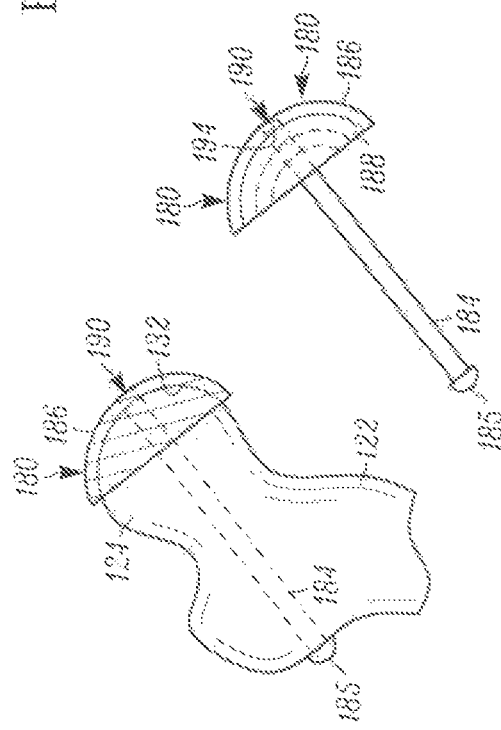
FIG. 11E illustrates the femur of FIG. 3 with a view of the cup femoral head prosthesis and cannulated fastener both inside and outside the hip joint.
Figure 11A:
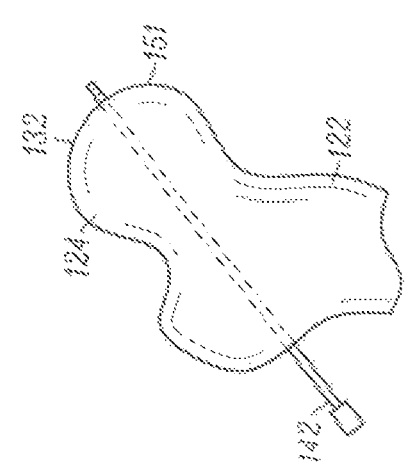
FIG. 11A illustrates the femur of FIG. 3 with the guide wire positioned therein.

As discussed above, various options exist for repairing or replacing the hip joint 104 after preparation of the hip joint 104. Referring now to FIGS. 11A-11E, in at least some embodiments, a cup femoral head prosthesis 180 can be installed on the femoral head 124. This procedure includes securing the cup femoral head prosthesis 180 to the femoral head 124. As seen in FIG. 11A, the guide wire 142 is positioned through the femur 122. In at least some embodiments, to fasten the cup femoral head prosthesis 180, a cannulated drill 181 is rotated over the guide wire 142, as seen in FIG. 11B, until it passes out of the femoral head outer surface 132 at the center 170 of the femoral head 124. The guide wire 142 is secured and the cup femoral head prosthesis 180 is brought into the hip joint 104 through the midanterior portal 108. The guide wire 142 is then articulated with the cup femoral head prosthesis 180, while a cannulated fastener, such as a cannulated screw 184 with an anchoring head 185, is inserted into the femur 122 over the guide wire 142, as seen in FIG. 11C. Further, as seen in FIG. 11C, the cup femoral head prosthesis 180 is illustrated. The cup femoral head prosthesis 180 can include numerous shapes, for example a shape similar to the hemiarthroplasty cup 172, such as a hemispherical, partially hemispherical, or substantially hemispherical cup shape. The cup femoral head prosthesis 180 includes a femoral cup outer surface 186 and a femoral cup inner surface 188.

The cup femoral head prosthesis 180 can be utilized with or without the hemiarthroplasty cup 172. As such, if a hemiarthroplasty cup 172 is not to be installed, the femoral cup outer surface 186 is shaped and sized to pivotably engage the acetabulum outer surface 130 (as seen in FIG. 8) after it has been reamed. If the hemiarthroplasty cup 172 is to be installed, the femoral cup outer surface 186 is shaped and sized to pivotably engage the cup inner surface 176 of the hemiarthroplasty cup 172. The femoral cup inner surface 188 is shaped and sized to fit the end 151 of the femoral head outer surface 132, after it has been reamed. The cup femoral head prosthesis 180 further includes a fastener receiving aperture 190 (see FIG. 11E) for engaging the cannulated screw 184. In at least some embodiments, the receiving aperture 190 extends there through and includes threads 194 for engaging a threaded end portion 196 of the cannulated screw 184.

Figure 12:
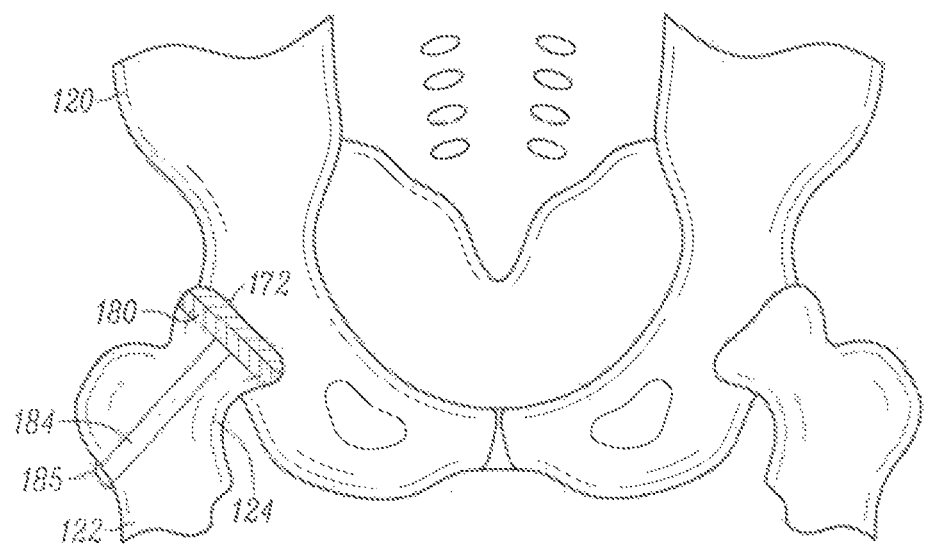
FIG. 12 illustrates a view of the hip joint of FIG. 2, post-installation of the cup femoral head prosthesis and the hemiarthroplasty cup prosthesis.
Figure 11D:
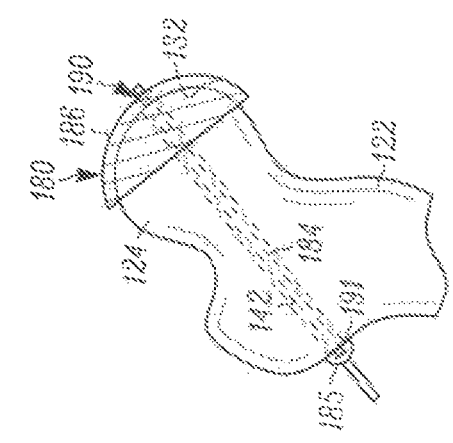
FIG. 11D illustrates the femur of FIG. 3 with the cup femoral head prosthesis secured to the femur.

Referring to FIG. 11D, the cup femoral head prosthesis 180 is positioned over the femoral head outer surface 132 and the cannulated screw 184 is secured to the cup femoral head prosthesis 180. In at least some embodiments, this is accomplished by rotating the cannulated screw 184 to engage the threaded end portion 196 with the receiving aperture 190 and tightening of the cannulated screw 184 until the anchoring head 185 is secured against a lateral femoral cortex 191 of the femur 122, and the cup femoral head prosthesis 180 is secured onto the femoral head outer surface 132. Once installed, the cup femoral head prosthesis 180 provides a smooth and secure pivoting surface. After the fastening has begun or has been completed, the guide wire 142 can be removed, as seen in FIG. 11E. In at least some embodiments, the installation of the cup femoral head prosthesis 180 is followed by the insertion of the hemiarthroplasty cup 172 into the hip joint 104, where the hemiarthroplasty cup 172 can be brought into the hip joint 104 through the midanterior portal 108. Upon completion of the installation of the prosthesis, the traction is taken off the hip joint 104 and the cup femoral head prosthesis 180 is brought to articulate with the hemiarthroplasty cup 172, as seen in FIG. 12.

The cup femoral head prosthesis 180 and the hemiarthroplasty cup 172 can be utilized together, or in isolation as a hemiarthroplasty. In addition, the cup femoral head prosthesis 180 and the hemiarthroplasty cup 172 can be utilized together, or in isolation, without performing a reaming procedure on a joint. The cup femoral head prosthesis 180 is comprised of materials suitable for insertion into the body 102, such as cobalt chrome, steel, aluminum, and/or other alloys, metals, ceramics, polymer composites, etc. The femoral cup inner surface 188 of the cup femoral head prosthesis 180 can be comprised of a porous, grit blasted, or otherwise oriented surface amenable to either ongrowth or ingrowth of the bone from the femoral head outer surface 132. In addition, the hemiarthroplasty cup 172 is comprised of materials suitable for insertion into the body 102, such as polyethylene, cobalt chrome, steel, aluminum, and/or other alloys, metals, ceramics, or polymer composites. The aforementioned material lists are not exclusive and therefore, other materials not listed or currently unknown can be used if suitable for such a purpose. Although the aforementioned procedure is described in relation to hip joint 104, the components and procedures can be modified to accommodate repair and/or replacement of various other joints in the human body, such as a shoulder joint. For example, the shape of the reamer 150 could be modified to ream other ball and socket joints. Further, the components and procedures can be modified to accommodate repair and/or replacement of a hip joint or other joints in the body of an animal as well.

Figure 13:
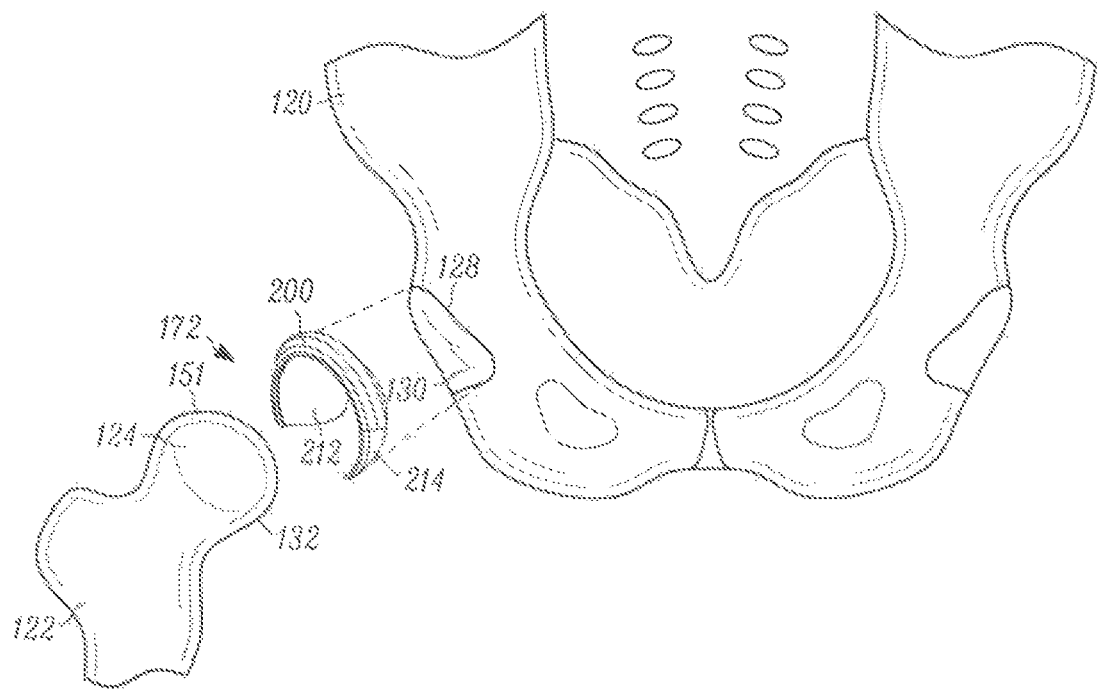
FIG. 13 illustrates the femur and pelvis of FIG. 3 and an exemplary joint spacer.
Figure 14:
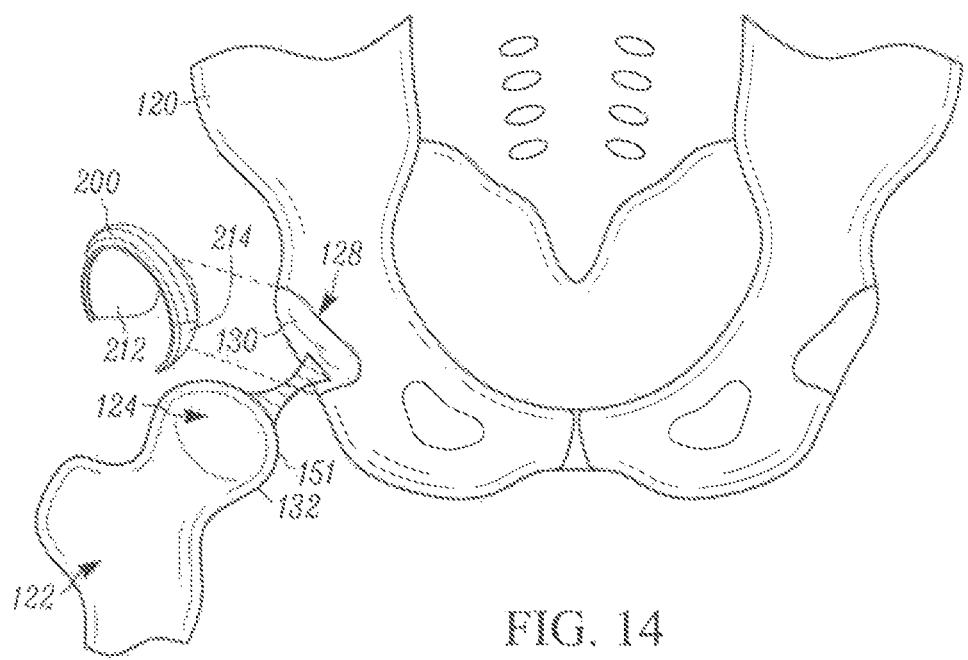
FIG. 14 illustrates the femur and pelvis of FIG. 3 with an attached ligamentum teres ligament and an exemplary joint spacer.

Referring to FIG. 13, a view of the hip joint 104 of FIG. 2 with the femur 122 distracted from the pelvis 120 and an exemplary joint spacer 200 shown there between is provided. The spacer 200 can be used as a joint replacement or enhancement device, where the term "joint replacement" is to be understood as including a wide variety of uses in arthroplasty procedures, some which may include, among other things, partial or complete joint replacement. As noted above, the hip joint 104 includes at least portions of the pelvis 120 and the femur 122. The femur 122 includes the femoral head 124 connected to the femur 122 by the femoral neck 126. The pelvis 120 includes the acetabulum socket 128. The distraction exposes the acetabulum outer surface 130 and the femoral head outer surface 132. The acetabulum outer surface 130 and femoral head outer surface 132 are at least partially comprised of a layer of articular cartilage 141. FIG. 14 also illustrates a view of the hip joint 104, but with a ligamentum teres ligament 210 attached to the acetabulum outer surface 130 and femoral head outer surface 132.

In at least some embodiments, the spacer 200 is configured for positioning between the acetabulum outer surface 130 and the femoral head outer surface 132. As shown in FIG. 15, the spacer 200 includes an inner surface 212 configured to accommodate at least one of a portion of the femoral head outer surface 132 and a prosthetic secured to the femoral head 124. As shown in FIG. 16, the spacer 200 includes an outer surface 214 configured to accommodate at least one of a portion of the acetabulum outer surface 130 and a prosthetic secured to the pelvis 120. In at least some embodiments, the inner surface 212 and outer surface 214 have similar contours providing a uniform thickness, while in other embodiments, they may have dissimilar contours providing a varying thickness across the spacer 200. The thickness between the inner surface 212 and outer surface 214 can vary, although in at least some embodiment, the thickness is about 2 millimeters to about 8 millimeters, while in other embodiments the thickness is about 4 millimeters, while in further embodiment, the thickness can be greater or less than 2-8 millimeters. In at least some embodiments, the spacer 200 has a circular curvilinear shape with an inner perimeter 216 and an outer perimeter 218. The inner perimeter 216 and outer perimeter can be continuous to form closed inner and outer circles, or in other embodiments, they can be discontinuous, wherein the inner perimeter 216 is joined to the outer perimeter 218 to form a posterior limb 220 and an anterior limb 222. The inner perimeter 216 can be smaller in length relative to the outer perimeter 218. In at least some embodiments, the posterior limb 220 is wider than the anterior limb 222, although in other embodiments, they can be the same or otherwise different. The spacer 200 includes an interior perimeter diameter 223 that extends between opposite sides of the inner perimeter 216. In at least some embodiments, the interior perimeter diameter 223 can range from about 40 millimeters to about 60 millimeters, while in other embodiments, the interior perimeter diameter 223 can be greater or less than 40-60 millimeters, while in further embodiments, the interior perimeter diameter 223 can range from about 30 millimeters to about 70 millimeters For descriptive purposes, the spacer 200 can be identified as having at least three portions, a posterior portion 230, an anterior portion 232, and a superior portion 234. Additionally, the superior portion 234 can be further identified as having a posterior superior portion 236 and an anterior superior portion 238. In at least some embodiments, the spacer 200 can include a lip 240 that extends outwardly from the outer perimeter 218 along the superior portion 234, although in other embodiments, the lip 240 can extend along the entire outer perimeter or a smaller portion thereof, including or excluding any portion of the superior portion 234. The lip 240 includes an inner edge 242 that is joined to the outer perimeter 218, wherein the lip 240 extends radially from and along the outer perimeter 218 forming a lip extension 246 that terminates along an outer edge 244, a first side edge 248, and a second side edge 250. The lip extension 246 further includes a top surface 252 and a bottom surface 254, wherein in at least some embodiments, the bottom surface 254 is configured to at least partially abut a portion of the acetabulum socket 128. In some embodiments, the lip 240 will be unsecured to the acetabulum socket 128, while in other embodiment, the lip 240 can be secured to the acetabulum socket 128 using a fastener, such as a screw, adhesive, etc. The each of the dimensions of the lip 240 can vary as desired to accommodate fitment to a particular joint or patient. Although the lip 240 is illustrated as a rectangular arc with generally flat surfaces, the lip 240 can vary in shape, for example, circular, triangular, parabolic, sinusoidal, etc., and can have a varied cross-section to include non-flat surfaces.

The lip 240 can provide numerous functions, such as engaging a portion of the acetabulum outer surface 130 when unsecured, and as a securement means to provide a securing point. To assist with securement of the lip 240 to the acetabulum socket 128, in at least some embodiment, the lip extension 246 can be trefinated, so as to include one or more holes (not shown). The holes can vary in size and spacing as desired, although in at least some embodiments, the holes can be about 2-3 millimeters in diameter and about 8 millimeters apart. The holes can then be utilized with a fastener, such as a screw, peg, staple, or a suture anchor. The femoral head can articular with the spacer 200 and the lip 240 would be included in the articulation.

FIGS. 15-19 illustrate an embodiment of the spacer 200 that is asymmetric and configured for use in the right side of a pelvis, and FIGS. 20-24 illustrate another embodiment, spacer 300, that is asymmetric and configured for use in the left side of a pelvis. It is to be understood, that either configuration can be modified as desired to be used on either side of the pelvis as well as to accommodate various other joints in the body of a mammal. Further it is to be understood that the spacer 300 is, in at least some embodiments, a mirror image of the spacer 200 and performs a similar function, but for an opposite joint, and therefore the description and operations provided for spacer 200 can be applied to the spacer 300 without the need for repetition throughout the specification.

As discussed above, the inner perimeter 216 and outer perimeter 218 can be discontinuous, thereby providing a gap 260 between the first end 220 (e.g., posterior limb 220) and the second end 222 (e.g., anterior limb 222). The gap 260 provides an opening for passing a ligament, such as the ligamentum teres ligament 210, therethrough. For example, as shown in FIG. 14, the ligament 210 is secured at either end to the acetabulum outer surface 130 and femoral head outer surface 132, as it naturally occurs. The gap 260 allows the spacer 200 to at least partially surround the ligament with the inner perimeter 216. In this manner, the ligament 262 can remain attached, thereby avoiding the trauma associated with the need to cut off the ligament, which is required when installing a hemispherical cup or other cup shaped prosthesis that lacks an opening to accommodate the existing ligament. This represents a substantial improvement over the prior art, allowing for procedures to repair a damaged joint without inflicting substantial invasive trauma. This substantially improves healing time and future mobility, as well as the strength of the repaired joint, as opposed to procedures that require the removal or cutting of the ligament securing the joint. In addition, as in at least some embodiments, the spacer 200 includes an inner perimeter and is not a closed back cup type configuration, the spacer 200 requires less material to be inserted into the body and the removal of less bone material from the body, thereby mitigating the need to modify the joint and add new matter to the body. The dimensions of the spacer 200 can be varied to accommodate the shape of the acetabulum and femoral head patient (or the shape of other joints if not the hip joint) of a specific patient. In this manner, the overall size of the spacer 200 can be limited so as to replace only the necessary portions of the joint that are damaged, as opposed to a standard cup shape found in the prior art, which generally requires a gross modification of the joint to accommodate an extensive implant. This also contributed to recovery and future mobility. The information for the desired dimensions can be obtained using one or more of various diagnostic tools, such as a radiograph, a CT scan, an MM, or an equivalent modality.

In at least some embodiments, the spacer 200 can be installed where the ligament 210 has been removed. In such an installation, the unique shape of the spacer allows for expanded articulation of the joint. Further, where the ligament 210 is not attached, the inner and outer diameters of the spacer 200 can be continuous to provide an "O" shape, as opposed to a "U" shape.

The spacer 200 is comprised of materials suitable for insertion into the body 102, such as polyethylene, plastic, rubber, cobalt chrome, steel, aluminum, and/or other alloys, metals, ceramics, polymer composites, cadaveric tissue, living tissue (e.g., dermis), etc. The aforementioned material lists are not exclusive and therefore, other materials not listed or currently unknown can be used if suitable for such a purpose. Portions of the spacer 200 can be comprised of one or more different materials. For example, the lip 240 can be comprised of a material different than the outer surface 214 or inner surface 212. In addition, the surfaces of the spacer 200, for example, the outer surface 214 or inner surface 212 can include one or more different topographical surfaces, such as ribbed, dimpled, textured, grit blasted, etc. In at least some embodiments, the outer surface 214 utilizes a material or texture that is advantageous to biological securement to the acetabulum socket 128 via bone growth, while the inner surface 212 includes a material and texture that allows smooth articulation with the femoral head 124. Further, the rigidity of the spacer 200 can vary, as a whole, as well as among portions of the spacer 200. For example, the lip 240 can be more flexible than the remaining portion of the spacer 200. The outer surface 214 of the spacer 200 can be comprised of a porous, grit blasted, or otherwise oriented surface amenable to either ongrowth or ingrowth of the bone from the acetabulum socket 128. Although the aforementioned procedure is described in relation to hip joint 104, the components and procedures can be modified to accommodate repair and/or replacement of various other joints in the human body, such as a shoulder joint. Further, the components and procedures can be modified to accommodate repair and/or replacement of a hip joint or other joints in the body of an animal as well. In at least some embodiments, the spacer 200 is configured to be wetable. In at least some embodiments, the device is configured to be installed to an unprepared joint, or a prepared or reamed joint. The spacer 200 can also be utilized with various other prosthetics, such as, a hemi-arthroplasty prosthetic femoral head.

It is specifically intended that the aforementioned spacers 200 and 300 not be limited to the embodiments and illustrations contained herein, but include modified forms of those embodiments including portions of the embodiments and combinations of elements of different embodiments as come within the scope of the following claims. Further, the steps outlined above can be modified in various manners, such as performance in one or more alternate orders. The addition or exclusion of any step(s) discussed or not discussed, does not preclude a desired completion of the procedure.

What is claimed is:

1. A joint replacement device comprising:
   an asymmetric spacer configured for positioning within an acetabulum socket, the spacer including:
   an inner surface configured to accommodate at least one of a portion of an outer surface of a femoral head of a femur and a prosthetic secured to the femoral head;
   an outer surface configured to accommodate at least one of a portion of an outer surface of an acetabulum socket and a prosthetic secured to a pelvis, wherein the inner surface and outer surface each have a circular curvilinear shape and together include an inner perimeter and an outer perimeter, and wherein the inner perimeter is joined to the outer perimeter to form a posterior limb and an anterior limb;
   an interior perimeter diameter that extends between opposite sides of the inner perimeter; and
   a posterior portion, an anterior portion, and a superior portion formed from the inner surface and the outer surface;
   wherein the superior portion further includes a posterior superior portion and an anterior superior portion;
   wherein the inner perimeter and the outer perimeter are discontinuous, thereby providing a gap between the posterior limb and the anterior limb that leads to an opening configured to allow the passage of a ligament therethrough; and
   wherein the opening extends through the inner and outer surfaces of the spacer and is asymmetrically positioned such that a center of the opening is offset from a centerline of the spacer.

2. The device of claim 1, further comprising a lip that extends outwardly from the outer perimeter along the superior portion.

3. The device of claim 2, wherein the lip includes an inner edge that is joined to the outer perimeter, wherein the lip extends radially from and along the outer perimeter forming a lip extension that terminates along a lip outer edge, a lip first side edge, and a lip second side edge.

4. The device of claim 3, wherein the lip extension further includes a top surface and a bottom surface, and wherein the bottom surface is configured to at least partially abut a portion of the acetabulum socket when installed.

5. The device of claim 4, wherein the lip is configured to be unsecured to the acetabulum socket.

6. The device of claim 4, wherein the lip is configured to be secured to the acetabulum socket using a fastener.

7. The device of claim 1, wherein the interior perimeter diameter ranges from about 30 millimeters to about 70 millimeters.

8. The device of claim 1, wherein the inner perimeter is smaller in length relative to the outer perimeter.

9. The device of claim 1, wherein the posterior limb has a greater width than the anterior limb.

10. The device of claim 1, wherein the anterior limb has a width equal to the posterior limb width.

11. The device of claim 1, wherein the inner surface and the outer surface have similar contours providing a uniform thickness.

12. The device of claim 1, wherein the inner surface and the outer surface have dissimilar contours providing a varying thickness.

13. The device of claim 1, wherein the thickness between the inner surface and the outer surface is about 2 millimeters to about 8 millimeters.

14. The device of claim 1, wherein the interior perimeter diameter ranges from about 30 millimeters to about 70 millimeters.

15. An asymmetrically-shaped spacer configured for positioning within an acetabulum socket, the spacer comprising:

an inner surface configured to accommodate at least one of a portion of an outer surface of a femoral head of a femur and a prosthetic secured to the femoral head;

an outer surface configured to accommodate at least one of a portion of an outer surface of an acetabulum socket and a prosthetic secured to a pelvis, wherein the inner surface and outer surface each have a circular curvilinear shape and together include an inner perimeter and an outer perimeter, and wherein the inner perimeter is joined to the outer perimeter to form a posterior limb and an anterior limb;

an interior perimeter diameter that extends between opposite sides of the inner perimeter;

a posterior portion, an anterior portion, and a superior portion formed from the inner surface and the outer surface, wherein the superior portion further includes a posterior superior portion and an anterior superior portion; and a lip that extends outwardly from the outer perimeter along the superior portion, wherein the lip includes an inner edge that is joined to the outer perimeter, and wherein the lip extends radially from and along the outer perimeter forming a lip extension that terminates along a lip outer edge, a lip first side edge, and a lip second side edge;

wherein the inner perimeter and the outer perimeter are discontinuous, thereby providing a gap between the posterior limb and the anterior limb that leads to an opening configured to allow the passage of a ligament therethrough; and wherein the opening extends through the inner and outer surfaces of the spacer and is asymmetrically positioned relative to the lip such that a center of the opening is offset from a centerline of the lip.

16. An asymmetrically-shaped spacer configured for positioning within an acetabulum socket, the spacer comprising:

an inner surface configured to accommodate at least one of a portion of an outer surface of a femoral head of a femur and a prosthetic secured to the femoral head;

an outer surface configured to accommodate at least one of a portion of an outer surface of an acetabulum socket and a prosthetic secured to a pelvis, wherein the inner surface and outer surface each have a circular curvilinear shape and together include an inner perimeter and an outer perimeter, and wherein the inner perimeter is joined to the outer perimeter to form a posterior limb and an anterior limb;

an interior perimeter diameter that extends between opposite sides of the inner perimeter;

a posterior portion, an anterior portion, and a superior portion formed from the inner surface and the outer surface, wherein the superior portion further includes a posterior superior portion and an anterior superior portion; and a lip that extends outwardly from the outer perimeter along the superior portion, wherein the lip includes an inner edge that is joined to the outer perimeter, and wherein the lip extends radially from and along the outer perimeter forming a lip extension that terminates along a lip outer edge, a lip first side edge, and a lip second side edge;

wherein the inner perimeter and the outer perimeter are discontinuous, thereby providing a gap between the posterior limb and the anterior limb that leads to an opening configured to allow the passage of a ligament therethrough; and wherein the opening extends through the inner and outer surfaces of the spacer and is asymmetrically positioned such that a center of the opening is offset from a centerline of the spacer.

17. The spacer of claim 16, wherein the lip extension further includes a plurality of fastener apertures configured to receive a fastener for securing the lip to the acetabulum socket.

* * * * *